United States Patent
Patwardhan

(10) Patent No.: US 12,350,063 B2
(45) Date of Patent: *Jul. 8, 2025

(54) ENHANCING PIGMENTATION IN DERMOSCOPY IMAGES

(71) Applicant: Canfield Scientific, Incorporated, Parsippany, NJ (US)

(72) Inventor: Sachin V. Patwardhan, Mount Tabor, NJ (US)

(73) Assignee: Canfield Scientific, Incorporated, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/111,538

(22) Filed: Feb. 18, 2023

(65) Prior Publication Data

US 2023/0190180 A1    Jun. 22, 2023

Related U.S. Application Data

(63) Continuation of application No. 16/183,659, filed on Nov. 7, 2018, now Pat. No. 11,612,350.

(Continued)

(51) Int. Cl.
*A61B 5/00* (2006.01)
*A61B 5/103* (2006.01)
(Continued)

(52) U.S. Cl.
CPC ............ *A61B 5/443* (2013.01); *A61B 5/0013* (2013.01); *A61B 5/0077* (2013.01);
(Continued)

(58) Field of Classification Search
CPC ..... A61B 5/443; A61B 5/0013; A61B 5/0077; A61B 5/1032; A61B 5/444; A61B 5/742;
(Continued)

(56) References Cited

U.S. PATENT DOCUMENTS 7,515,952 B2 *  4/2009  Balas ................. A61B 5/0084
                                                         359/368
9,355,466 B2 *  5/2016  Kakinuma ........... H04N 1/6075
(Continued)

OTHER PUBLICATIONS

Tsumura et al., Image-based skin color and texture analysis/synthesis by extracting hemoglobin and melanin information in the skin, 2003, ACM SIGGRAPH 2003 Papers, pp. 770-779 (Year: 2003).*

*Primary Examiner* — Rochelle D Turchen

(57) ABSTRACT

Methods and apparatuses are disclosed for modifying images of skin so as to reduce or enhance the appearance of component pigments, such as melanin and hemoglobin. A diffuse reflectance image of skin, such as a cross-polarized contact dermoscopy image, which conveys information regarding subsurface features of the skin, is processed so as to extract pigment distribution information, which is then used to correct the diffuse reflectance image, such as by reducing the appearance of melanin to allow better visualization of hemoglobin-related structures, such as vasculature. Alternatively, the diffuse reflectance image can be corrected so as to reduce the appearance of hemoglobin to allow better visualization of melanin-related structures.

20 Claims, 5 Drawing Sheets

Related U.S. Application Data

(60) Provisional application No. 62/582,904, filed on Nov. 7, 2017.

(51) Int. Cl.
*G06T 5/94* (2024.01)
*G06T 7/00* (2017.01)
*G06T 7/90* (2017.01)
*H04N 1/60* (2006.01)
*H04N 9/64* (2023.01)
*H04N 23/10* (2023.01)
*H04N 23/56* (2023.01)
*G02B 27/28* (2006.01)

(52) U.S. Cl.
CPC ............ *A61B 5/1032* (2013.01); *A61B 5/442* (2013.01); *A61B 5/444* (2013.01); *A61B 5/742* (2013.01); *G06T 5/94* (2024.01); *G06T 7/0012* (2013.01); *G06T 7/90* (2017.01); *H04N 1/6052* (2013.01); *H04N 9/646* (2013.01); *H04N 23/10* (2023.01); *H04N 23/56* (2023.01); *A61B 2576/02* (2013.01); *G01N 2800/207* (2013.01); *G02B 27/288* (2013.01); *G06T 2207/10024* (2013.01); *G06T 2207/20092* (2013.01); *G06T 2207/30088* (2013.01)

(58) Field of Classification Search
CPC ....... G06T 7/0012; G06T 7/90; H04N 1/6052; H04N 9/646; H04N 23/10; H04N 23/56
See application file for complete search history.

(56) References Cited

U.S. PATENT DOCUMENTS

| | | | |
|---|---|---|---|
| 2011/0206254 A1* | 8/2011 | Patwardhan | A61B 5/441 382/128 |
| 2015/0087902 A1* | 3/2015 | Mertz | A61B 1/044 600/109 |
| 2016/0166194 A1* | 6/2016 | Gareau | A61B 5/14552 600/328 |
| 2019/0117147 A1* | 4/2019 | Kikuchi | A61B 5/1032 |

* cited by examiner

ENHANCING PIGMENTATION IN DERMOSCOPY IMAGES

RELATED APPLICATIONS

This application is a continuation of and claims the benefit under 35 U.S.C. § 120 of U.S. patent application Ser. No. 16/183,659 filed Nov. 7, 2018, which is incorporated herein by reference in its entirety and which claims priority from U.S. Provisional Patent Application No. 62/582,904, filed Nov. 7, 2017, also incorporated herein by reference in its entirety.

BACKGROUND INFORMATION

Dermoscopy is the analysis of the primary morphology of microscopic subsurface skin structures that are not visible to the unaided eye. When examining a skin lesion, a physician will typically evaluate the presence or absence of specific colors and/or structures, color and structure distribution, and whether the structure morphology is typical/regular versus atypical/irregular. A contact cross-polarized image is often used for such an evaluation.

Nuances of color are important when evaluating a lesion. The colors the physician tries to identify and distinguish are Black, Brown, Gray, Blue, White, Red, Pink, and Yellow. Of these colors, Black, Brown, Gray, Blue, and White are associated with melanin distribution and its sub-surface depth. In dermoscopy images, melanin in the outer epidermal layer and throughout the epidermis will appear Black. At the epidermal-dermal junction, melanin will appear Brown, with darker shades being associated with higher concentrations. In the mid-reticular to upper dermis, melanin may appear Gray-Blue or Gray-Black, and in the papillary or reticular dermis melanin will appear Blue. Red and shades of Pink are associated with vascularity or bleeding within the lesions. White color is associated with regression and scarring. Yellow color is associated with stratum corneum devoid of blood and melanin.

Identifying pigmentation patterns and their distribution are also important when evaluating a lesion. For melanin hypo- or hyper-pigmented structures, the patterns commonly evaluated, for example, are reticular, globular, streaks, dots, pseudopods, spoke-wheel, leaf-like, etc. Vascular patterns evaluated, for example, are dotted, arborizing, corkscrew, crown, comma-like, etc. A combination of certain patterns, including the presence or absence of patterns and their symmetry/uniformity, and the distribution of colors helps the physician identify the type of skin lesion and whether it is cancerous, atypical, or benign. Part of the examination process also involves identifying the lesion's boundary while evaluating its color and pattern distributions. Separating melanin structures from vascular structures, visualizing and identifying patterns in dark areas (due to concentration or depth of the pigment in these areas), and demarcating the lesion boundary, especially when the lesion is non-melanocytic, atypical, or cancerous, can be extremely challenging, even with good quality, contact cross-polarized dermoscopic imaging. The challenge is even greater with imaging arrangements in which the illumination and image capture environment is less well-controlled, as is typical, for example, of conventional reflectance imaging.

Conventional reflectance imaging of skin typically entails illuminating the skin with white light and capturing the light reflected therefrom. (A conventional reflectance image may also be referred to as a standard captured image, or a total reflection image among other commonly used terms.) The reflected light has two components: a specular or surface reflection component, and a diffuse reflection component. When separated from each other, each component provides useful information about the imaged tissue. The surface reflection component is useful for analyzing topological characteristics of tissue such as surface texture and visible features such as wrinkles and pores. The diffuse reflection component, which is due to light that has interacted with the tissue interior, conveys information about the optical properties of the tissue such as the distribution of chromophores like melanin and hemoglobin. Some photons of the incident light penetrate within the tissue and undergo multiple scattering and absorption events before some of those photons are back-scattered as diffuse reflected light. The average penetration depth of a photon is dependent on its wavelength, with longer-wavelength photons penetrating deeper into the tissue. The wavelength- or color-dependent penetration depth of photons is illustrated in FIG. 1.

Cross-polarized and parallel-polarized imaging have been the preferred techniques used for respectively capturing diffuse and surface reflection components independently. In a typical arrangement, illustrated in FIG. 1, a broad-band light source 10 illuminates an area of skin while images are captured using a digital color camera 20 with polarizing filters 15, 25 in both the illumination and reflection paths. For capturing diffuse reflection images, the polarization axes of filters 15, 25 are oriented orthogonal to each other. A part 51 of the polarized incident light 50 is reflected back from the skin surface. This surface reflection component 51 maintains the same polarization as that of the incident light 50 and is blocked by the detector side polarizing filter 25 due to its orthogonal orientation relative to filter 15 in the illumination path. Another part 52 of the polarized incident light 50 penetrates the skin surface and undergoes multiple scattering and absorption events before some of those photons are back-scattered as diffuse reflected light 53. Due to scattering, the diffuse reflected light 53 has lost all its polarization and hence a portion thereof is able to pass through the detector side polarizing filter 25. For capturing surface reflection images, the polarization axes of the filters 15, 25 are oriented parallel to each other.

Diffuse reflection images can also be captured using a dark field illumination technique where the light is incident at an angle only on the edge of the skin area being imaged while the detector is allowed to capture only reflected light which is almost perpendicular to the skin surface. Although dark-field illumination techniques do not require polarizing filters, they have several drawbacks. The angle of illumination is dependent on the area being illuminated. If the angle of incidence is too shallow or too direct, then there will be a dark spot in the center where no light has reached. The area that can be imaged is very small since it will have a radius equal to the average of the total scattering length of the light in tissue. Some form of a ring light source of appropriate diameter is thus required.

Diffuse reflection images of skin can also be obtained, with or without polarization, using a contact plate with a refractive index matching fluid, such as oil, water and/or alcohol, applied between the plate and the skin being imaged. In addition to requiring the application of fluid to the skin surface, the fluid may have bubbles which will obscure information and can fog the view, among potential drawbacks.

Diffuse reflection images of skin, regardless of how they are obtained, can be analyzed in order to evaluate tissue pigmentation and distribution information. Evaluation of diffuse reflection color images for tissue pigmentation information can be carried out using various tools such as color-space transformations, various combinations of color-spaces, optical models of light-tissue interaction, treating the color channels of the images as multi-spectral measurements, Principal Component Analysis (PCA), or Independent Component Analysis (ICA), with or without linear or non-linear tissue absorption models.

Another technique for evaluating tissue pigmentation is the RBX technique which can transform Red/Green/Blue (RGB) diffuse reflectance skin images into Red and Brown representations indicative of hemoglobin and melanin distributions, respectively. (See R. Demirli et al., "RBX Technology Overview", Canfield Imaging Systems, February 2007; and U.S. Pat. No. 8,498,460, incorporated herein by reference in its entirety.) In an implementation of the RBX technique, an RGB cross-polarized image of skin is transformed to a Red/Brown/X (RBX) color-space using a combination of a light transport model of skin and a spectral-dependent model of the source-detector configuration used in capturing the RGB image. The RBX color-space transformation is based upon random samplings of cross-polarized skin images obtained from a large population of subjects with different skin types.

Due to restrictions on imaging geometry, image acquisition and processing, quality of image acquisition and illuminating optical components, polarizing filter misalignment, and/or calibration errors, it may not always be possible to capture a pure diffuse reflection image using cross-polarized imaging. The quality of the cross-polarized data tends to degrade for shallow angles of illumination or near-perpendicular angles for detection with respect to the imaging surface, such as when capturing multiple images from various angles for 3D imaging using stereo techniques. When the field-of-view is large, cross-polarization is compromised as one moves away from the central axis of the imaging plane. Cross-polarization is also compromised if the area being imaged is not flat but has appreciable curvature. The resultant data in either case is similar to that of a standard captured image, which has both specular and diffuse reflection information. This limits the ability to obtain tissue pigmentation information using techniques such as those mentioned.

Good quality cross-polarized images can be obtained with contact dermoscopy and closed imaging systems such as Canfield Scientific's VISIA imaging systems, which provide a well-controlled illumination and image capture environment. Such cross-polarized images are of sufficient quality for obtaining good tissue pigmentation information using techniques such as those mentioned. Without such systems, however, it is not typically possible to obtain diffuse reflection images of sufficient quality from which good tissue pigmentation information can be extracted.

SUMMARY OF THE DISCLOSURE

The present disclosure sets out a method performed by a skin imaging apparatus comprising: obtaining a diffuse reflectance image of an area of skin; determining a pigment component of the image; modifying the image by reducing or enhancing the appearance of the pigment component in the image; and causing the modified image to be displayed, stored, transmitted or further processed.

The present disclosure also sets out a skin imaging apparatus comprising: a storage device containing instructions; and a processor executing the instructions to: obtain a diffuse reflectance image of an area of skin; determine a pigment component of the image; modify the image by reducing or enhancing the appearance of the pigment component in the image; and cause the modified image to be displayed, stored, transmitted or further processed.

These and other aspects of such apparatuses and methods and exemplary variants thereof are described in greater detail below.

DETAILED DESCRIPTION

Figure 1:
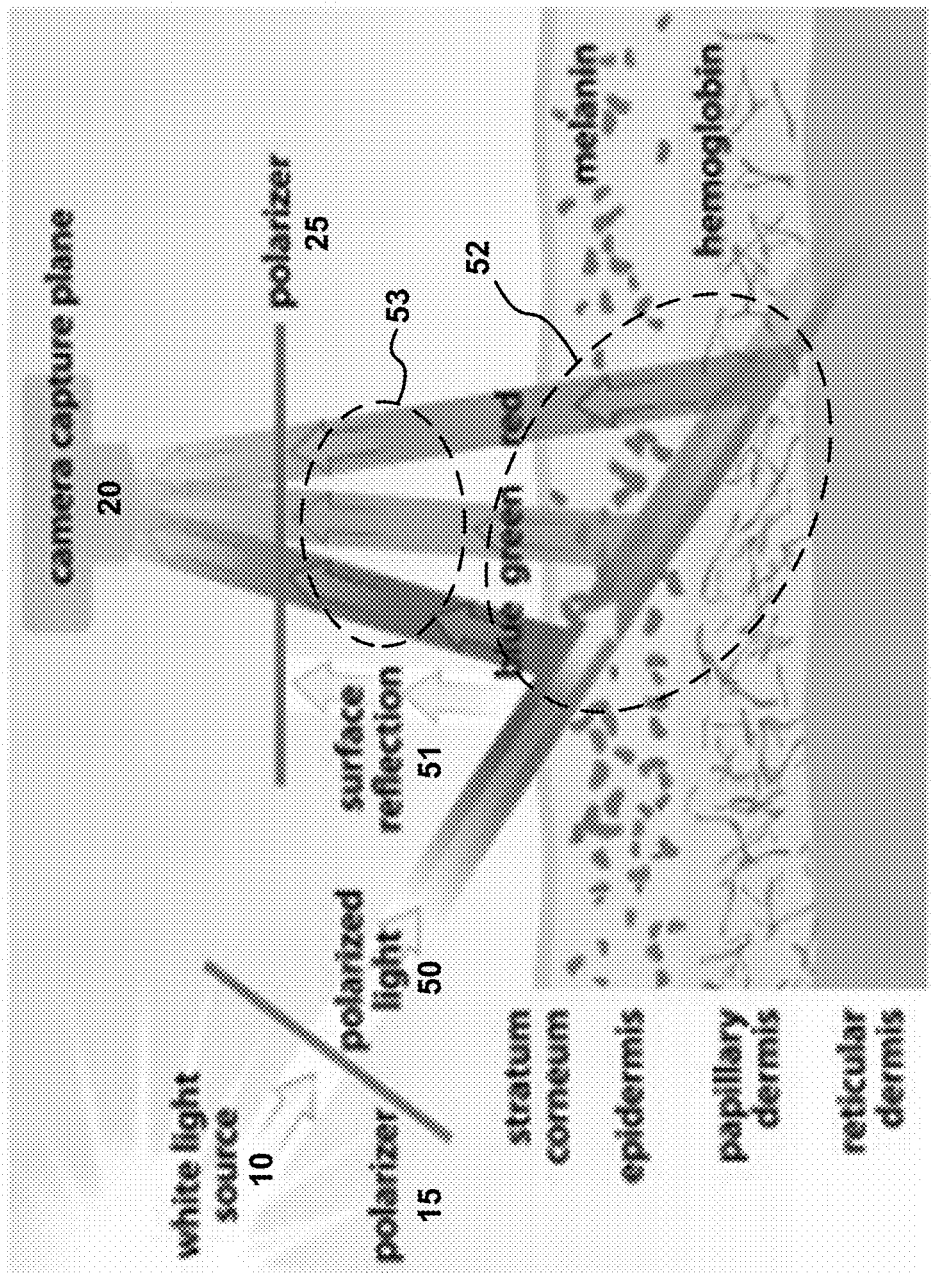
FIG. 1 illustrates the interaction of light with the structures of typical skin in a polarized image capture arrangement.

The following merely illustrates the principles of the disclosure. It will thus be appreciated that those skilled in the art will be able to devise various arrangements which, although not explicitly described or shown herein, embody the principles of the disclosure and are included within its spirit and scope. More particularly, while numerous specific details are set forth, it is understood that embodiments of the disclosure may be practiced without these specific details and in other instances, well-known circuits, structures and techniques have not been shown in order not to obscure the understanding of this disclosure.

Furthermore, all examples and conditional language recited herein are principally intended expressly to be only for pedagogical purposes to aid the reader in understanding the principles of the disclosure and the concepts contributed by the inventor(s) to furthering the art and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, and the like represent various processes which may be substantially represented in computer readable medium and so executed by a computer or processor, whether or not such computer or processor is explicitly shown.

The functions of the various elements shown in the drawings, including any functional blocks, steps, procedures, modules, units or the like may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, dedicated circuitry, digital signal processor (DSP) hardware, network-based processors, application specific integrated circuitry (ASIC), read-only memory (ROM), random access memory (RAM), and non-volatile storage. Other hardware, conventional and/or custom, may also be included.

Software modules, or simply modules which are implied to be software, may be represented herein as any combination of flow chart elements or other elements indicating performance of process steps and/or textual description. Such modules may be executed by hardware that is expressly or implicitly shown. Additionally, although illustrated as single elements, each such block or step shown may be implemented with multiple blocks or steps, or various combinations thereof. Terms such as "software," "application," "program," "firmware," or the like, are intended to refer, without limitation, to any instruction or set of instructions, structure, or logic embodied in any suitable machine-readable medium.

As used herein, the term "image" may encompass any form of photo-documentation, including 2D images and/or 3D surfaces and/or 3D volumetric image data, where a 2D image could be a single or a multichannel visible impression obtained by a camera, a 3D surface could be points in a 3D space connected by line segments to form a polygonal mesh along with any associated 2D images that represent the underlying texture and a 3D volumetric image data might represent a stack of 2D images that represent a 3D volume of the object being imaged.

Skin features or pathological conditions may include, for example, wrinkles, spots, pores, scars, tattoos, moles, skin lesions, nevi, acne, etc.

Figure 2:
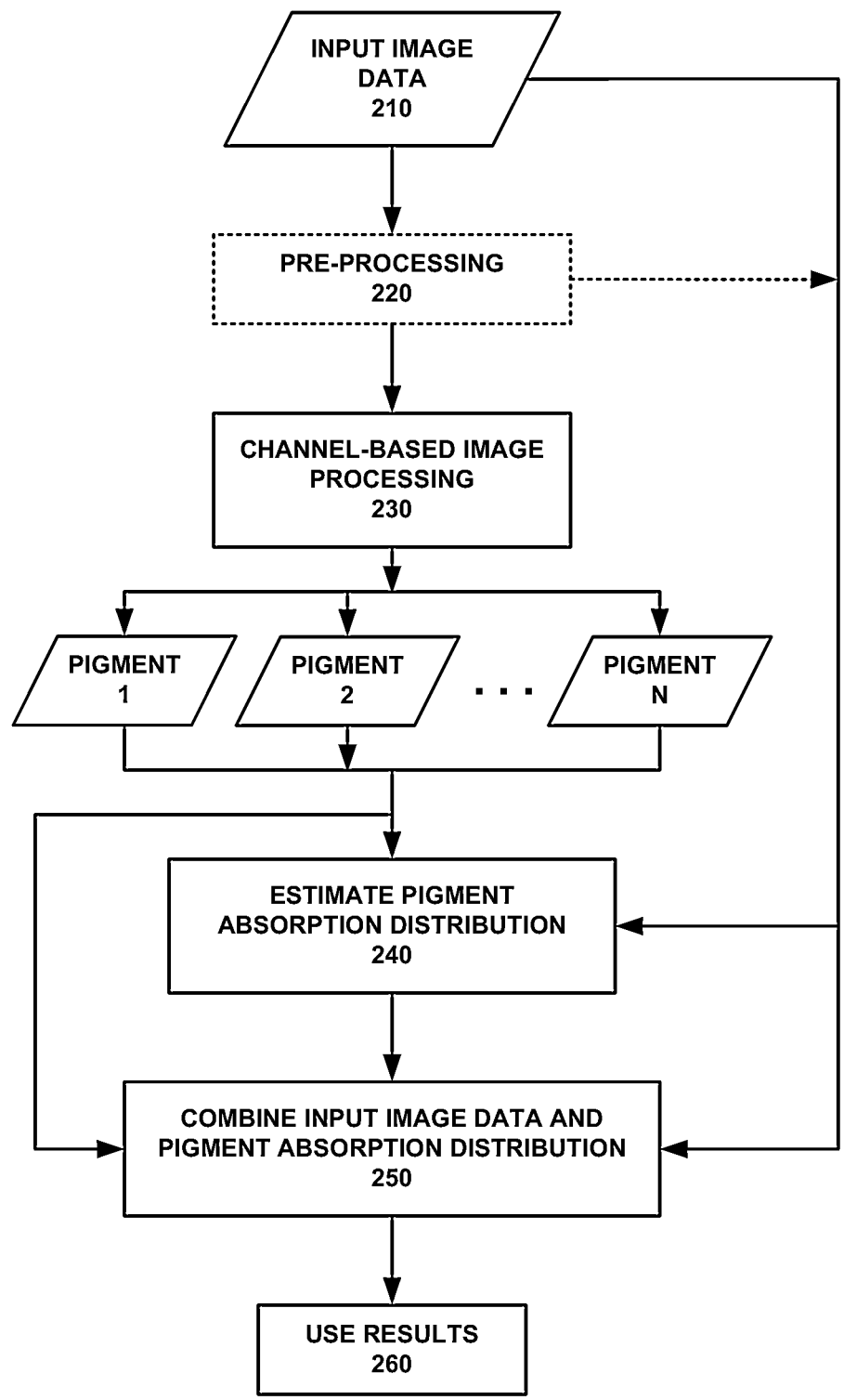
FIG. 2 is a flow chart illustrating an exemplary method in accordance with the present disclosure.

An exemplary method in accordance with the present disclosure will now be described with reference to FIG. 2, which shows a representation thereof in the form of a flow chart. As shown in FIG. 2, method 200 uses diffuse reflectance image data 210 as input. Input image data 210 can be from a single image or a sequence of images, such as a recorded or live video. In exemplary embodiments, it is contemplated that the input diffuse reflectance image data 210 is obtained from contact or non-contact, cross- or non-polarized images; i.e., contact cross-polarized, contact non-polarized, non-contact cross-polarized, or non-contact non-polarized images. It is also contemplated, in exemplary embodiments, that the images are Red/Green/Blue (RGB) images, illuminated by white light, as typically captured with conventional digital photography. As will be appreciated, however, images represented in other color spaces or formats can also be used in exemplary embodiments.

At 220, the input image data 210 can then be subjected to optional pre-processing, which may include one or more of: color correction; conversion to a three-channel RGB image format, including Bayer filter de-mosaicing, if the input data is in a raw format; color balance; gamma correction; and/or conversion to 8- or 16-bit format, among other possible operations. Additionally, if the light distribution of the imaging device is not uniform (for example there is a gradient from the center going radially outwards in a dermatoscope), pre-processing may also include correcting for such lighting issues.

After the optional pre-processing 220, the input image data is subjected to channel-based image processing at 230 in order to extract one or more components of the image representative of skin pigments, such as hemoglobin and melanin. Such processing may include RBX transformation, Independent Component Analysis (ICA), Principal Component Analysis (PCA), and/or color space transformations, such as transforming the input image data from the RGB to the Lab color space and using the color channels or a combination to produce melanin or hemoglobin distribution images. Pigment distribution images produced by the processing 230 are used to generate a corrected or modified version of the original image, as described further below.

In exemplary embodiments, RBX processing is used at 230 to represent skin images in terms of melanin and hemoglobin components. Application of RBX techniques to a cross-polarized Red/Green/Blue (RGB) image of skin transforms the image into a Red/Brown/X (RBX) colorspace, in which the Red and Brown channels represent hemoglobin and melanin distributions, respectively and the X channel typically represents scattering and light distribution. When a technique such as RBX is used to transform a good quality diffuse reflectance skin image, such as a contact cross-polarized dermoscopic image, in addition to separating the image into hemoglobin (RBX-Red) and melanin (RBX-Brown) distributions, it is also possible to further separate the melanin distribution into darker colored melanin appearing Black or Blue-Gray, and lighter colored melanin appearing various shades of Brown. These two types are referred to herein as RBX-Brown-1 and RBX-Brown-2, respectively. Because a contact cross-polarized image is essentially a pure diffuse reflectance image, the third independent component X generated by the RBX transform of such an image is representative of the additional Brown component.

In an illustrative implementation of the method of FIG. 2, three pigment components are determined at 230, namely, hemoglobin, Black/Blue-Gray melanin, and Brown melanin.

At 240, using the pigment distribution information obtained as a result of the image processing at 230 and with a knowledge of each pigment's spectral- or color-dependent absorption properties, an estimation is performed of how much the particular pigment has affected the Red (R), Green (G), and Blue (B) color components (or channels) and intensity of the input image 210. Both melanin and hemoglobin have specific spectro-colorimetric light absorption properties, which can be represented as color information. The estimation of pigment absorption distribution at 240 can be carried out for pigments either individually or in combination, depending on which pigments are to be enhanced or suppressed. Exemplary procedures that can be used at 240 to estimate pigment absorption distribution will now be described with reference to FIGS. 3A and 3B.

Figure 3A:
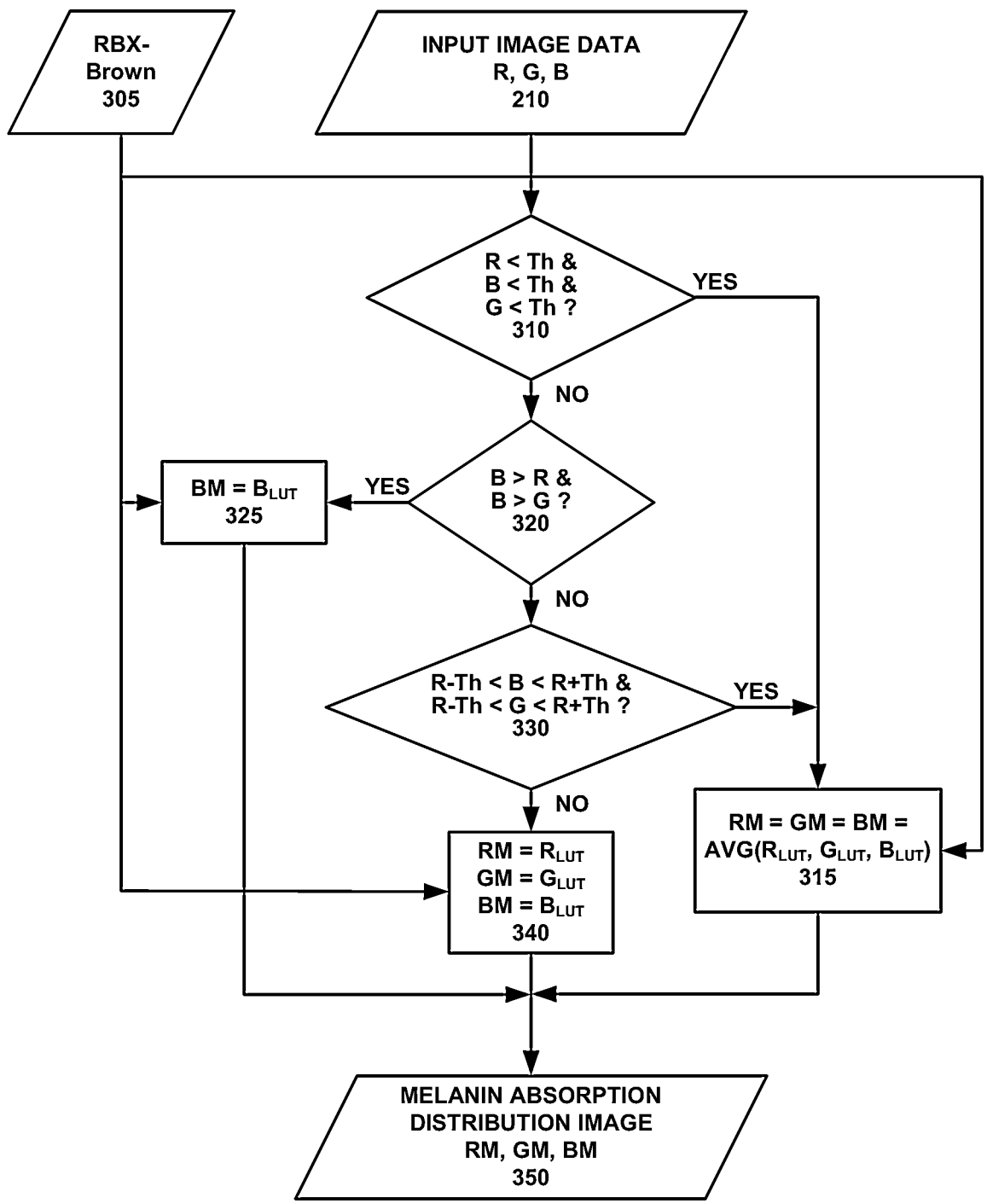
FIGS. 3A and 3B are flow charts illustrating exemplary methods of determining pigment absorption distribution information in accordance with the present disclosure.

FIG. 3A is a flowchart depicting an exemplary procedure that uses RBX-Brown information 305 generated at 230 and input image data 210 to estimate melanin absorption distribution, or in other words, to generate a melanin absorption distribution image 350. As described more fully below, the exemplary procedure entails the application of a set of rules on the colors detected in the input image data 210 to determine how to estimate the color of the melanin component therein.

As shown in FIG. 3A, the R, G and B components of each pixel of the input image data 210 are compared at 310 to a small threshold value Th (e.g., 10 for an 8-bit range of 0-255). If all three components of a pixel of the input image data 210 are determined to be below the threshold value, it is deemed that the pixel is Black, which is indicative of superficial/epidermal melanin. If so, operation proceeds to 315 in which the R, G and B components (RM, GM, and BM) of the corresponding pixel in the resultant melanin absorption distribution image 350 are set in accordance with a color look-up table (LUT) that provides an estimated color of melanin based on its concentration.

As discussed above, for good quality diffuse reflectance images, the RBX technique can distinguish between darker colored melanin appearing Black or Blue-Gray (Brown-1), and lighter colored melanin appearing various shades of Brown (Brown-2). While the RBX technique provides the concentration of each of these types of melanin, which can be depicted as grayscale images, the grayscale image of the Brown-2 component can be translated into a color image, as follows:

TABLE 1

| RBX-Brown-2 Grayscale | Melanin Concentration | Estimated Melanin Color |
|---|---|---|
| 0 | High | Dark Brown |
| 1-254 | Mid | Progressively lighter shades of Brown as RBX-Brown-2 grayscale increases |
| 255 | Low | White |

Table 1 describes an RBX-Brown look-up table (RBX-Brown LUT) that provides a set of RGB values, RLUT, GLUT and BLUT for each grayscale value indicative of the concentration of melanin at a pixel. The RBX-Brown LUT can be generated based on training data, for example.

At 315, for the case of an input image pixel deemed to be Black, RM, GM, and BM of the resultant melanin absorption distribution image 350 are each set to the average of RLUT, GLUT and BLUT obtained from the LUT for the melanin concentration value of the corresponding pixel of the RBX-Brown-2 grayscale image 305 generated at 230.

If, however, it is determined at 310 that the pixel of the input image data 210 is not Black, operation proceeds to 320, in which the B component of the pixel is compared to the pixel's R and G components. If the B component is greater than both the R and G components, it is deemed that the pixel is Blue, which is indicative of deeper/dermal melanin. In that case, at 325, the B component BM of the melanin absorption distribution image 350 is set to BLUT obtained from the LUT for the melanin concentration value of the corresponding pixel of the RBX-Brown-2 grayscale image 305 generated at 230. The components RM and GM are preferably set to zero, so as not to alter the appearance of vascular information.

If, however, it is determined at 320 that the pixel of the input image data 210 is not Blue, operation proceeds to 330, in which the B and G components of the pixel are compared to the R component to determine whether they are relatively close to the R component (i.e., within some relatively small range of +/−Th.) If so, the pixel is deemed to be Gray, which is indicative of dermal melanin. In that case, RM, GM, and BM of the melanin absorption distribution image 350 are each set at 315 to the average of RLUT, GLUT and BLUT obtained from the RBX-Brown LUT for the melanin concentration value of the corresponding pixel of the RBX-Brown-2 grayscale image 305.

If, however, it is determined at 330 that the pixel of the input image data 210 is not Gray, operation proceeds to 340, in which RM, GM, and BM of the melanin absorption distribution image 350 are set to RLUT, GLUT and BLUT, respectively, as provided by the RBX-Brown LUT for the melanin concentration value of the corresponding pixel of the RBX-Brown-2 grayscale image 305. In this case, the pixel is deemed to be Brown, which is indicative of epidermal-dermal junction melanin which appears various shades of Brown in accordance with concentration.

Figure 3B:
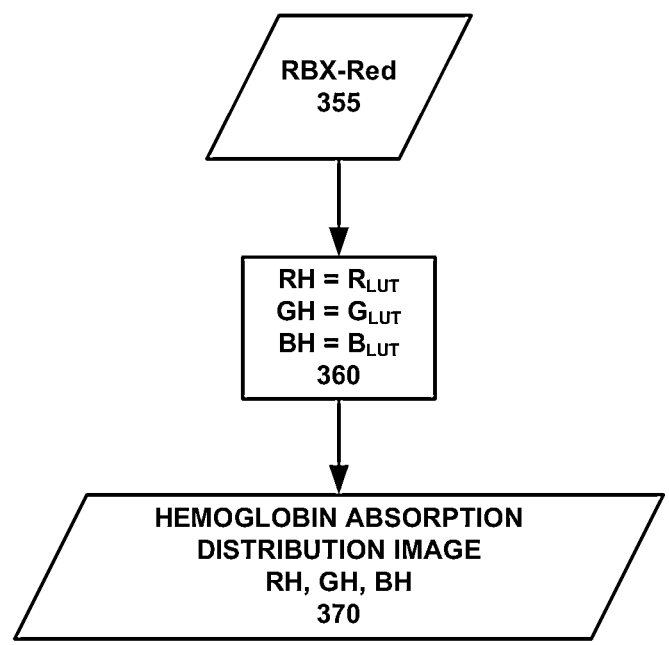

An analogous procedure can be performed at 240 for the pigment hemoglobin. FIG. 3B is a flowchart depicting an exemplary procedure that uses RBX-Red information 355 generated at 230 to estimate hemoglobin absorption distribution, or in other words, to generate a hemoglobin absorption distribution image 370.

As in the case of melanin, while the RBX technique provides the concentration of hemoglobin as the component RBX-Red, which can be depicted as a grayscale image, this grayscale image can be translated into a color image, as follows:

TABLE 2

| RBX-Red Grayscale | Hemoglobin Concentration | Estimated Hemoglobin Color |
|---|---|---|
| 0 | High | Dark Red |
| 1-254 | Mid | Progressively lighter shades of Red, Pink, as RBX-Red grayscale increases |
| 255 | Low | White |

Table 2 describes an RBX-Red look-up table (RBX-Red LUT) that provides a set of RGB values, RLUT, GLUT and BLUT for each grayscale value indicative of the concentration of hemoglobin at a pixel. The RBX-Red LUT can be generated based on training data, for example.

As shown in FIG. 3B, at 360, the R, G and B components (RH, GH, and BH) of the corresponding pixel in the hemoglobin absorption distribution image 370 to be generated, are set in accordance with the RBX-Red LUT. In other words, RH, GH, and BH of the hemoglobin absorption distribution image 370 are set to RLUT, GLUT and BLUT, respectively, as provided by the RBX-Red LUT for the hemoglobin concentration value of the corresponding pixel of the RBX-Red grayscale image 355.

Returning now to FIG. 2, the input image 210 (or preprocessed image 220) is then corrected at 250 using the one or more pigment absorption distributions estimated at 240 so as to reduce or enhance the influence of the respective one or more pigments. In exemplary implementations, the modification carried out at 250 entails combining the input image data 210 and the pigment absorption distributions estimated at 240 through mathematical operation (addition/subtraction, multiplication/division, etc.)

For example, the influence of melanin on the input image can be enhanced or reduced to generate a corrected image in accordance with the following operations:

Corrected image Red=Input image Red+$d \times RM$,

Corrected image Green=Input image Green+$d \times GM$,

Corrected image Blue=Input image Blue+$d \times BM$, (1)

where RM, GM and BM are the RGB components of the melanin absorption distribution image determined at 240, such as described above, and d (having a range of −1.0 to +1.0, for example) indicates the degree of enhancement or reduction of the influence of melanin on the input image. The value of d can be user-selected for example.

Image correction can also be achieved by dividing the R, G, and B color channels of the input image 210 by a certain proportion or percentage of the RBX-Brown image, such as in accordance with the following operations:

Corrected image Red=Input image Red/($e \times RM$),

Corrected image Green=Input image Green/($e \times GM$),

Corrected image Blue=Input image Blue/($e \times BM$), (2)

where e (having a range of 0.01 to 100.0, for example) indicates the degree or extent of enhancement or reduction of the influence of melanin on the input image.

As can be appreciated, the choice of image correction operations, e.g., (1) or (2), employed at 250 can be based on the format of the input image data 210 and of the pigment absorption distribution image. Additionally, in order to avoid falling out of the range of displayable values (e.g., 0-255 range for 8-bit values) the corrected image component data resulting from the correction operations may be subjected to re-scaling, while ensuring that the dynamic range of the original image is maintained so as to avoid the corrected image appearing darker or brighter than the original image.

A corrected image, with the influence of melanin reduced or eliminated, provides better visualization and identification of vascular structures and patterns as well as of deeper melanin. Since superficial melanin appears black, it will obscure the structures and patterns of deeper melanin components. As such, by separating the superficial and deeper components of melanin, as is possible when applying the RBX technique to a good quality diffuse reflectance image, it is possible to better visualize the deeper melanin patterns and distributions by removing or reducing at 250 the influence of the superficial melanin from the input image 210.

A similar technique can be used to reduce or enhance the influence of hemoglobin in the input image to generate a corrected image for better visualization and identification of melanin structures and patterns. In the case of hemoglobin, the hemoglobin absorption distribution image 370, generated as described above with reference to FIG. 3B, can be combined with the R, G, and B color channels of the input image, similarly to the operations (1) and (2) set forth above for the case of melanin.

In exemplary implementations, the pigment colors can be calculated or weighted based on the subject's skin type. This information can be reflected in the RBX-Brown and RBX-Red LUTs, discussed above. Skin type can be specified, such as by user input, for example, or estimated by the system from normal skin within the image being processed.

Preferably, embodiments of the present disclosure enable a user to select the pigment distributions to be suppressed or enhanced, and/or to select the degree of suppression or enhancement to be applied. Consider, for example, a Canfield Scientific VEOS DS3 device configured in accordance with the present disclosure, displaying a live view of a cross-polarized video input image and presenting a GUI slider widget, or the like, by which the user can select the degree of suppression or enhancement, while viewing the resultant processed image.

The results output from 250, such as the corrected images, can then be used in one or more ways at 260, including, for example, displaying, storing, transmitting, and/or further processing the results. Further processing, may include, for example, compression, image segmentation, feature detection, or computation and output of one or more metrics, among other possibilities.

In further exemplary implementations, the combination of input image data 210 and pigment distribution information can be performed using image blending. More specifically, in such implementations, the input image 210 (or the pre-processed version thereof from 220) is blended with a percentage, preferably user-selectable, of a second image representative of the pigment distribution to be suppressed or enhanced in the input image. Image blending algorithms that can be used can be linear or non-linear and should take into account the dynamic range of both input images to avoid overflow. In an exemplary embodiment, an alpha-blending algorithm is used, in which the transparency (in a range of 0 to 1) of the image to be blended is specified.

The second image to be blended with the input image 210 can be obtained in a variety of ways.

As mentioned, where RBX processing is used at 230 to obtain pigment information, the Red and Brown data generated thereby is indicative of the concentration of hemoglobin and melanin, respectively, but does not include information about their relative RGB components. As mentioned, melanin near the skin's surface may appear Black, whereas more deeply situated melanin may appear Brown, Gray, or Blue, with increasing depth. Similarly, hemoglobin may appear dark Red to light Red, or Pink. The RGB components of the pigments whose concentrations are provided by RBX can be estimated based on those concentrations. In other words, pseudo-colored images of the melanin and hemoglobin distributions extracted from an input image can be generated by setting the RGB values of said images in accordance with the concentration information provided by the RBX technique. As described above, said RGB values can be provided, for example, in look-up tables or other suitable arrangements, whereby a set of values for the R, G and B components of the pigment color can be obtained for a given pigment concentration.

The RGB pigment image thus obtained, can then be blended at 250 with the input image 210.

Alternatively, instead of extracting pigment information from the input image data 210, with a technique such as RBX, a further input image can be obtained which has been captured at a selected wavelength or band of wavelengths and/or with illumination of a selected wavelength or band of wavelengths. The selected wavelengths can be those at which the absorption of a particular pigment is maximum or minimum. The two input images can then be blended, as described above, to reduce or enhance the appearance of the pigment.

Figure 4:
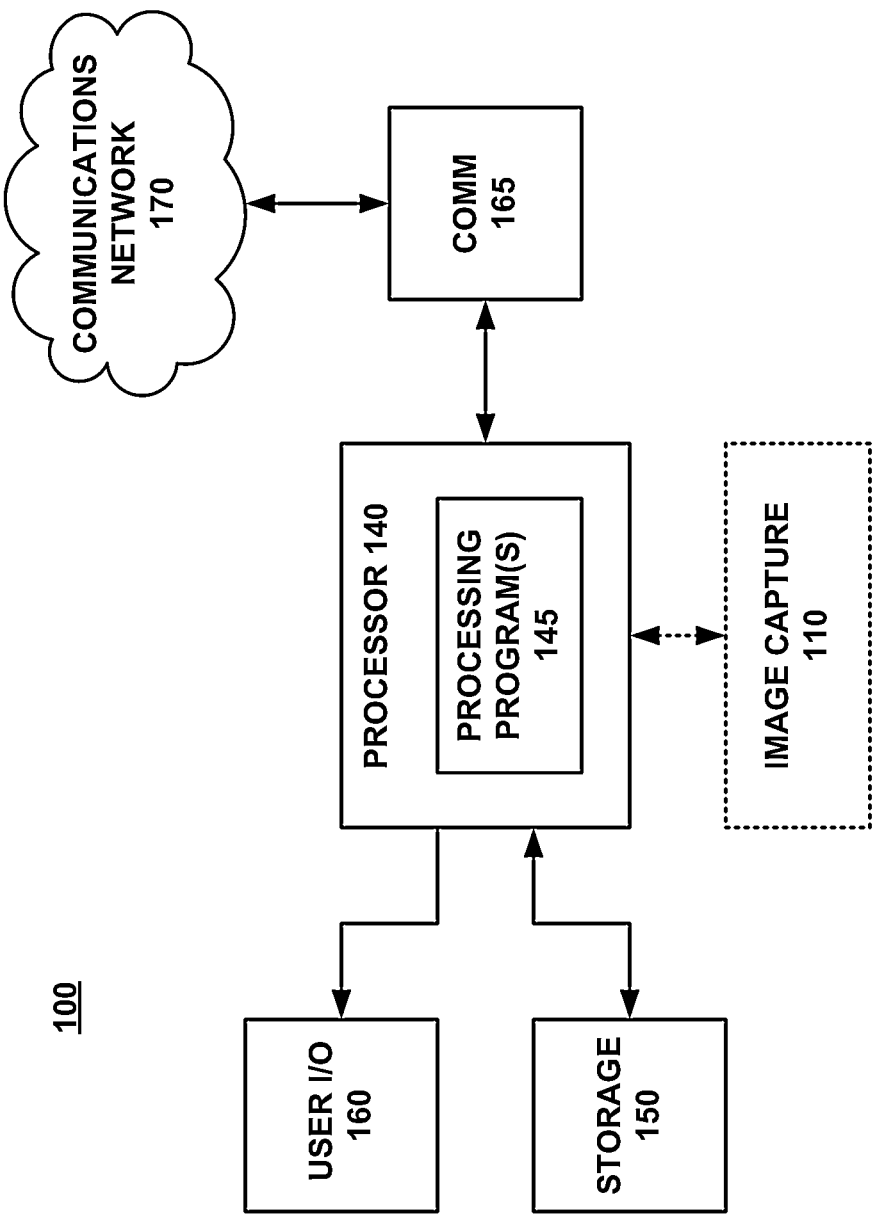
FIG. 4 is a schematic representation of an exemplary system in accordance with the present disclosure.

Turning now to FIG. 4, there is shown in schematic form an exemplary system 100 in accordance with the present disclosure. As shown in FIG. 4, system 100 may include an optional image capture system 110 coupled to a processor 140. Image capture system 110 may include one or more hand-held or mounted point-and-shoot or DSLR cameras, mobile cameras, frontal or rear-facing smart-device cameras, dermatoscopes (e.g., Canfield Scientific Inc.'s VEOS devices, and devices described in U.S. Patent Application Publication No. 20140243685 A1, incorporated herein by reference in its entirety), 2D skin imaging systems (e.g., Canfield Scientific Inc.'s VISIA), 3D human body imaging devices (e.g., Canfield Scientific Inc.'s VECTRA), and/or 3D Total Body systems (e.g., Canfield Scientific Inc.'s WB360, and systems described in U.S. Patent Application Publication No. 20180255292 A1, incorporated herein by reference in its entirety), and 3D volumetric imaging devices, among others.

Advantageously, the image capture system 110 is capable of capturing cross-polarized images, in which a polarizing filter in the viewing path of the image has a polarizing orientation orthogonal to that of polarized light emitted from a light source. One or more light sources may be integrated with the one or more image capture devices or implemented as separate components.

Images captured by image capture system 110 are provided to processor 140 for processing as described above. Processor 140 may also control image capture system 110, for example, by controlling one or more aspects of the image capture and/or illumination of the subject, such as exposure, modality, or filtering, among others.

Images may also be provided to processor 140 from other sources and by other means. For example, images may be provided via communications network 170, or in a non-transient storage medium, such as storage 150.

Processor 140 may be coupled to storage 150, for storing and retrieving images and parameters, among other data, and to input/output devices 160, such as a display device and/or user input devices, such as a keyboard, mouse, touchscreen, or the like. Processor 140 may also be coupled to a communications interface 165 for interconnection with a communications network 170, such as the Internet, for transmitting and receiving images and/or data, and/or receiving commands, software updates or the like. Processor 140, storage 150, I/O 160, and/or communications interface 165 may be implemented, for example, with one or more computers, workstations, tablet computers, smartphones, or the like, operating in accordance with one or more programs 145 embodied in a compatible, non-transient, machine-readable storage medium containing instructions for carrying out methods in accordance with the present disclosure, such as methods described above with reference to FIGS. 2, 3A and 3B.

It should be noted that the exemplary system 100 represents just one of a variety of possible arrangements contemplated by the present disclosure. For example, the various components of system 100 need not be co-located. For example, image capture system 110 and I/O devices 160 can be located in a dermatologist's office and processor 140 and storage module 150 can be remotely located, functioning within a tele-dermatology or "cloud-based" framework to interact with image capture system 110 and I/O devices 160 over communications network 170. In other exemplary arrangements, I/O devices 160 can be remotely located from image capture system 110, thereby allowing a dermatologist to remotely examine a subject's skin. In other embodiments, system 100 can be implemented using a conventional smartphone, tablet, or other suitable mobile computing device, in which image capture system 110, processor 140, storage 150, user I/O 160, and communications interface 165 are integrated in one housing, and in which one or more processing programs 145 in accordance with the present disclosure have been installed. The image capture system 110 of such a device can be modified or supplemented with cross-polarization optics and illumination. Alternatively, system 100 can be implemented using an integrated, hand-held device such as Canfield Scientific's VEOS DS3, which has cross-polarization imaging capabilities.

Uses and Applications

Some illustrative uses and applications of exemplary implementations in accordance with the present disclosure will now be described.

When performing a conventional whole-body skin examination, a physician moves a dermatoscope over a patient's skin surface while looking through the lens opening for identifying suspicious lesions, or so-called "ugly ducklings." The dermatoscope is preferably configured for cross-polarized viewing, in which a polarizing filter in the viewing path is orthogonally polarized to polarized light emitted from a light source, typically integrated with the dermatoscope. The dermatoscope may also have a camera attached thereto, allowing the physician to capture images for later evaluation.

In one application, the images captured with a conventional system, can be provided to a system such as system 100 and processed as described above. Interacting with the system, the physician can then perform an evaluation of the color and pigment structures in the captured images for classifying the lesions therein.

In another application, a similar examination can be carried out using the camera of a mobile device attached to a dermatoscope and looking at the screen of the mobile device. The examination can be performed from the live preview or by later reviewing a video captured by the device. Such operation can be performed using, for example, a Canfield Scientific Inc. VEOS HD1, HD2, or DS3 dermatoscope. When performing a whole-body examination while looking at the live preview, if the physician identifies a suspicious lesion, dermoscopy images of the lesion may be captured before continuing examination of remaining skin areas. In accordance with the present disclosure, frames of the live feed or video recorded during the examination can be processed in real-time to generate RBX images and corrected images. The physician has a choice of reviewing the as-captured images, an RBX image, or the corrected images, generated as described above. The physician may also choose to switch/toggle between these images when performing the examination. The original, RBX, and corrected images may be saved to a storage medium, displayed on an external monitor, transmitted to another location for remote review and examination, and/or processed further.

RBX pigment distribution images or the corrected image can be used for computer aided analysis and classification of the lesions. These images can be used for identifying pigment structure patterns or segmenting the lesion boundary. Preferably, the images can be displayed and reviewed as colored images or grayscale images depending on the user's choice.

At this point, while this disclosure has been presented using some specific examples, those skilled in the art will recognize that the teachings of this disclosure are not thus limited. The foregoing merely illustrates principles of the invention and it will thus be appreciated that those skilled in the art will be able to devise numerous alternative arrangements which, although not explicitly described herein, embody the principles of the invention and are within its spirit and scope. It is to be understood that numerous modifications may be made to the illustrative embodiments and that other arrangements may be devised without departing from the spirit and scope of the present invention as defined by the appended claims.

What is claimed:

1. A method performed by a processor of a skin imaging apparatus comprising:
   obtaining a diffuse reflectance image of an area of skin, the area of skin having been illuminated with polarized light of a first polarization orientation and the diffuse reflectance image having been captured through polarization of a second polarization orientation orthogonal to the first polarization orientation;
   extracting from the diffuse reflectance image a pigment component of the diffuse reflectance image, the pigment component being representative of a pigment in the area of skin;
   generating a pigment absorption distribution image in accordance with the pigment component;
   generating a modified diffuse reflectance image by selectively combining, in accordance with a user input, the diffuse reflectance image and the pigment absorption distribution image so as to selectively reduce or enhance an appearance of the pigment in the modified diffuse reflectance image; and causing the modified diffuse reflectance image to be displayed, stored, transmitted or further processed.

2. The method of claim 1 comprising pre-processing the image before determining the pigment component.

3. The method of claim 1 comprising:
receiving the user input, the user input indicating an extent of reducing or enhancing the appearance of the pigment,
wherein combining the diffuse reflectance image with the pigment absorption distribution image includes at least one of adding, subtracting, multiplying, or dividing the diffuse reflectance image and the pigment absorption distribution image in accordance with the extent indicated.

4. The method of claim 1, wherein the pigment absorption distribution image is generated in accordance with spectro-colorimetric light absorption properties of the pigment.

5. The method of claim 1, wherein obtaining the diffuse reflectance image includes:
illuminating the area of skin with the polarized light of the first polarization orientation; and
capturing the diffuse reflectance image through a polarized filter of the second polarization orientation.

6. The method of claim 1, wherein the pigment includes melanin or hemoglobin.

7. The method of claim 1, wherein:
determining the pigment component includes determining a concentration of the pigment; and
generating the pigment absorption distribution image includes setting a color of the pigment in the pigment absorption distribution image in accordance with the concentration of the pigment.

8. The method of claim 1, wherein determining the pigment component includes at least one of the following: a color space transformation, a Red/Brown/X transformation, an Independent Component Analysis, and a Principal Component Analysis.

9. The method of claim 1, wherein generating the modified diffuse reflectance image includes blending the diffuse reflectance image with the pigment absorption distribution image.

10. A non-transitory computer-readable storage medium having stored thereon a computer program comprising instructions for causing a skin imaging apparatus to perform the method of claim 1.

11. A skin imaging apparatus comprising:
a storage device configured to contain instructions; and
a processor configured to execute the instructions to:
obtain a diffuse reflectance image of an area of skin, the area of skin having been illuminated with polarized light of a first polarization orientation and the diffuse reflectance image having been captured through polarization of a second polarization orientation orthogonal to the first polarization orientation;
extract from the diffuse reflectance image a pigment component of the diffuse reflectance image, the pigment component being representative of a pigment in the area of skin;
generate a pigment absorption distribution image in accordance with the pigment component;
generate a modified diffuse reflectance image by selectively combining, in accordance with a user input, the diffuse reflectance image and the pigment absorption distribution image so as to selectively reduce or enhance an appearance of the pigment in the modified diffuse reflectance image; and
cause the modified diffuse reflectance image to be displayed, stored, transmitted or further processed.

12. The apparatus of claim 11, wherein the processor is configured to execute instructions to pre-process the diffuse reflectance image before determining the pigment component.

13. The apparatus of claim 11, wherein the processor is configured to execute instructions to:
receive the user input, the user input indicating an extent of reducing or enhancing the appearance of the pigment,
wherein combining the diffuse reflectance image with the pigment absorption distribution image includes at least one of adding, subtracting, multiplying, or dividing the diffuse reflectance image and the pigment absorption distribution image in accordance with the extent indicated.

14. The apparatus of claim 11, wherein the pigment absorption distribution image is generated in accordance with spectro-colorimetric light absorption properties of the pigment.

15. The apparatus of claim 11, comprising an image capture device including:
a light source for illuminating the area of skin with the polarized light of the first polarization orientation; and
a polarized filter of the second polarization orientation through which the diffuse reflectance image is captured.

16. The apparatus of claim 11, wherein the pigment includes melanin or hemoglobin.

17. The apparatus of claim 11, wherein:
determining the pigment component includes determining a concentration of the pigment; and
generating the pigment absorption distribution image includes setting a color of the pigment in the pigment absorption distribution image in accordance with the concentration of the pigment.

18. The apparatus of claim 11, wherein the processor is configured to execute instructions to determine the pigment component by at least one of the following: a color space transformation, a Red/Brown/X transformation, an Independent Component Analysis, and a Principal Component Analysis.

19. The apparatus of claim 11, wherein the processor is configured to execute instructions to generate the modified diffuse reflectance image by blending the diffuse reflectance image with the pigment absorption distribution image.

20. The method of claim 1, wherein:
the diffuse reflectance image and the pigment absorption distribution image are digital images including respective arrays of pixels, and
generating the pigment absorption distribution image includes:
comparing a color value of each pixel of the diffuse reflectance image to a threshold; and
setting a color value of each pixel of the pigment absorption distribution image in accordance with the comparison at the corresponding pixel of the diffuse reflectance image.

* * * * *